(12) United States Patent
Massaro

(10) Patent No.: US 8,544,348 B2
(45) Date of Patent: Oct. 1, 2013

(54) TUBE FOR SEPARATING PORTIONS OF A SAMPLE

(71) Applicant: Protedyne Corporation, Windsor, CT (US)

(72) Inventor: Peter Massaro, Burlington, CT (US)

(73) Assignee: Protedyne Corporation, Windsor, CT (US)

( * ) Notice: Subject to any disclaimer, the term of this patent is extended or adjusted under 35 U.S.C. 154(b) by 0 days.

(21) Appl. No.: 13/687,537

(22) Filed: Nov. 28, 2012

(65) Prior Publication Data

US 2013/0089475 A1    Apr. 11, 2013

Related U.S. Application Data

(63) Continuation of application No. 12/503,365, filed on Jul. 15, 2009, now Pat. No. 8,342,041.

(51) Int. Cl.
*G01N 1/22* (2006.01)
*G01N 1/18* (2006.01)

(52) U.S. Cl.
USPC ........................................ 73/863.21; 436/177

(58) Field of Classification Search
USPC ............... 73/864.51, 863.23, 863.21, 864.91; 604/403, 406, 409, 415, 416; 422/72, 73, 422/500, 506, 504, 527, 547–559; 436/45, 436/176–178
See application file for complete search history.

(56) References Cited

U.S. PATENT DOCUMENTS

| 5,084,240 | A | 1/1992 | Babson |
| 5,568,912 | A | 10/1996 | Minami et al. |
| 5,888,831 | A | 3/1999 | Gautsch |
| 7,824,611 | B2 * | 11/2010 | Buechler ..................... 435/287.1 |
| 8,342,041 | B2 | 1/2013 | Massaro |
| 2005/0136546 | A1 | 6/2005 | Berndt et al. |

(Continued)

FOREIGN PATENT DOCUMENTS

| EP | 0791394 A2 | 8/1997 |
| EP | 1547686 A1 | 6/2005 |
| EP | 1997557 A1 | 12/2008 |

OTHER PUBLICATIONS

International Report on Patentability and Written Opinion for International application No. PCT/US2010/001891, dated Jan. 17, 2012 (7 pages).

(Continued)

*Primary Examiner* — Daniel Larkin
*Assistant Examiner* — Jamar Ray
(74) *Attorney, Agent, or Firm* — Wolf, Greenfield & Sacks, P.C.

(57) ABSTRACT

A method and tube for separating a sample. The tube is configured to separate agglomerated or clumped material or other sample components having over a particular size from other smaller size portions of the sample. For example, blood clots may be separated from serum of a blood sample. The tube includes a chamber with a closed bottom and a sidewall extending upwardly from the bottom, and a sample inlet branch coupled to the chamber. A slit is positioned between the chamber and the sample inlet branch so that after a sample is placed into the sample inlet branch, a portion of the sample having a size smaller than the slit (e.g., liquid material) passes through the slit and into the chamber, and material in the sample having a size larger than the slit remains in the sample inlet branch.

19 Claims, 5 Drawing Sheets

(56) References Cited

U.S. PATENT DOCUMENTS

2006/0008387 A1 1/2006 Tansey
2006/0266969 A1 11/2006 Kawahara
2007/0217955 A1 9/2007 Kawahara

OTHER PUBLICATIONS

International Search Report, mailed Oct. 5, 2010, for International application No. PCT/US2010/001891.

* cited by examiner

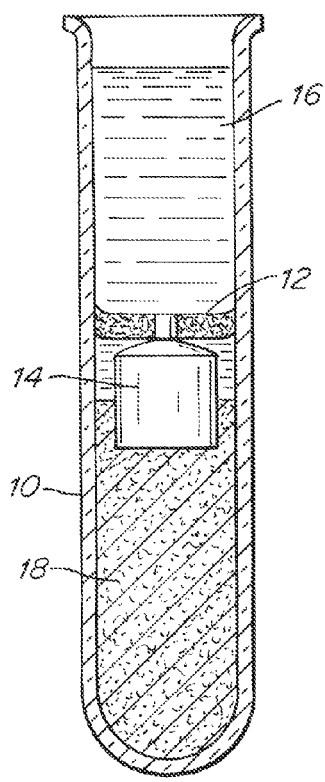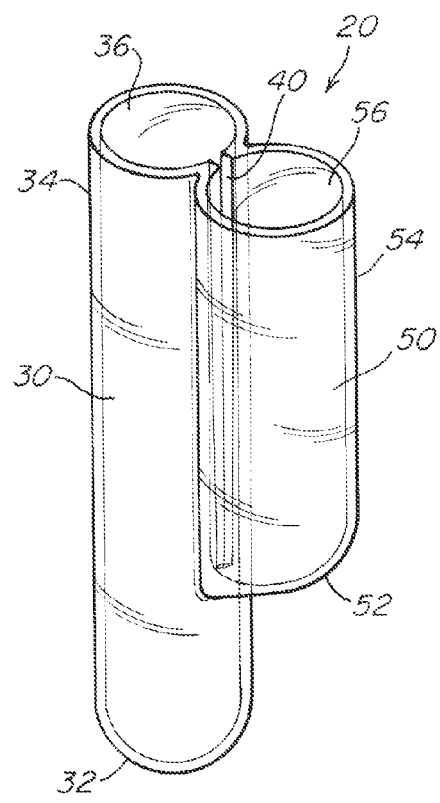
Fig. 1
(PRIOR ART)
Fig. 2

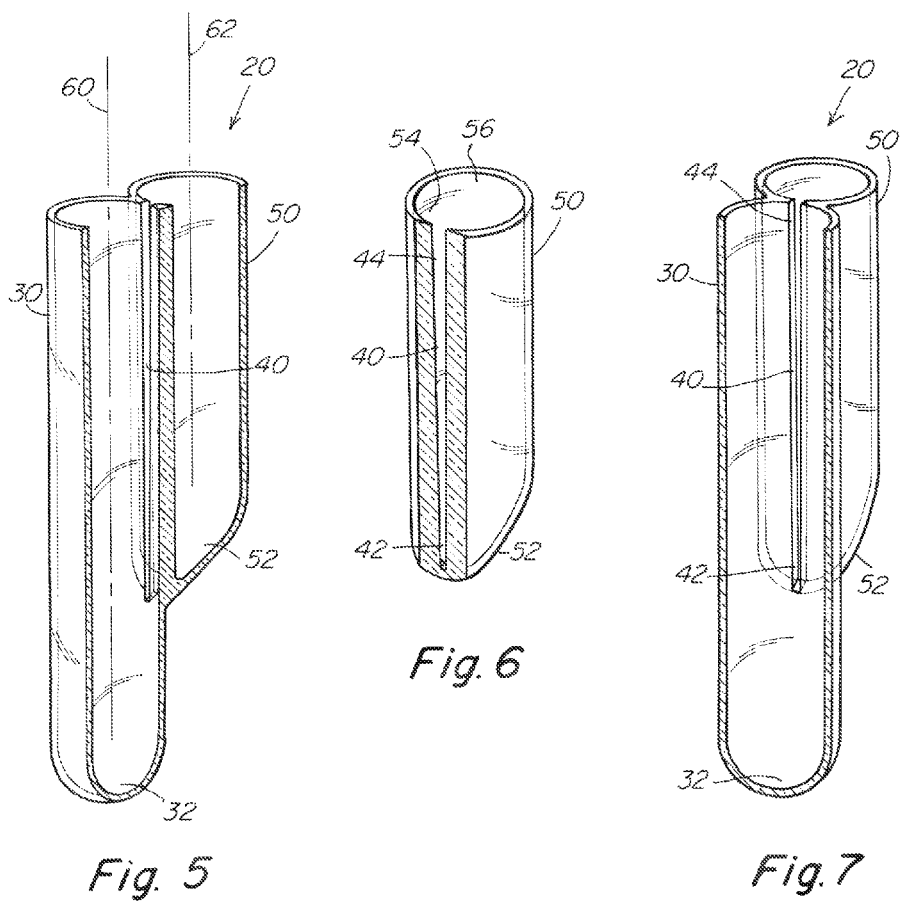

TUBE FOR SEPARATING PORTIONS OF A SAMPLE

RELATED APPLICATIONS

This application is a continuation of U.S. application Ser. No. 12/503,365, filed on Jul. 15, 2009, which is herein incorporated by reference in its entirety.

BACKGROUND

1. Field

The present application relates to a tube for separating portion of a sample including a liquid, and methods for using a tube to separate a sample.

2. Discussion of Related Art

In some liquid sample processing techniques, it is desirable to separate agglomerated, clotted or otherwise formed clumps of material from liquid and other small components in the sample. For example, clotting may occur in a blood sample after its removal from the body, and it may be desirable to separate fibrin or platelet clots from other portions of the blood sample (such as serum), whether the clotting occurs naturally or artificially such as in response to a reagent added to the sample.

Various devices are known to separate clumps of material from liquid portions of a sample. For example, one type of a device, known as a serum separator, is used to mechanically separate serum or plasma from other portions of a blood sample. One example of a serum separator is shown in FIG. 1 and includes a blood collection tube 10 with a cylindrical filter member 12 disposed within the tube. A weight 14 is attached to the filter member 12 so that the filter member moves down the tube and through the sample during centrifuging. The filter member is made from a material having pores which permit the passage of the liquid phase of a blood sample, but prevents the passage of the insoluble solid blood phase portion 18. As the filter member 12 moves down the tube 10, the serum or plasma 16 is forced through the pores of the filter element while particulates remain below the filter element in the solid phase portion 18.

SUMMARY OF INVENTION

Aspects of the invention provide a method and apparatus for separating portions of a sample including liquid. In one embodiment, the method and apparatus are configured to separate various types of clumps of material from the sample, e.g., blood clots, from other portions of a blood sample, such as blood serum. As discussed in greater detail below, in one embodiment, the method and apparatus are configured to be employed in high volume and/or automated liquid sample processing techniques.

According to one aspect of the invention, a tube for separating a liquid component from other portions of a sample includes a chamber having a closed bottom and a sidewall extending upwardly from the bottom. The sidewall defines a chamber opening for removing a separated liquid portion of the sample from the chamber. The tube also includes a sample inlet branch fluidly coupled to the chamber, and having a sidewall defining a sample inlet branch opening for dispensing an unseparated sample into the sample inlet branch. A slit may be positioned between the chamber and the sample inlet branch and arranged so that after the unseparated sample is dispensed into the sample inlet branch opening, a portion of the unseparated sample (e.g., serum having components with a size smaller than the slit) passes through the slit and into the chamber. Material in the unseparated sample having a size larger than the slit (e.g., blood clots of a blood sample) may remain in the sample inlet branch. As used herein, a "liquid portion" or "liquid component" of a sample may include only liquid, or liquid with solid particles that are suspended or otherwise carried by the liquid and are of a size small enough to pass through the slit between the sample inlet branch and the chamber.

According to another aspect of the invention, a method of separating a sample includes providing a tube having a chamber with a closed bottom and a sidewall extending upwardly from the bottom where the sidewall defines a chamber opening. The tube also has a sample inlet branch coupled to the chamber, with the sample inlet branch having a sidewall defining a sample inlet branch opening and a slit positioned between the chamber and the sample inlet branch. The method further includes placing an unseparated sample into the sample inlet branch opening, and passing a portion of the sample through the slit and into the chamber. Material in the unseparated sample having a size larger than the slit may remain in the sample inlet branch. The method also includes removing at least a portion of the separated sample from the chamber through the chamber opening.

These and other aspects of the invention are described below with reference to illustrative embodiments and in the claims. Various embodiments of the present invention provide certain advantages. Not all embodiments of the invention share the same advantages and those that do may not share them under all circumstances.

BRIEF DESCRIPTION OF THE DRAWINGS

The accompanying drawings are not intended to be drawn to scale. In the drawings, each identical or nearly identical component that is illustrated in various figures is represented by a like descriptor. For purposes of clarity, not every component may be labeled in every drawing.

Various embodiments of the invention will now be described, by way of example, with reference to the accompanying drawings, in which:

FIG. 1 is a front cross-sectional view of a prior art serum separator;

FIG. 2 is a perspective view of a tube for separating portions of a sample according to one embodiment of the present invention;

FIG. 5 is a perspective cross-sectional view taken along line 5-5 in FIG. 4;

FIG. 6 is a perspective cross-sectional view taken along line 6-6 in FIG. 4;

FIG. 7 is a perspective cross-sectional view taken along line 7-7 in FIG. 4;

DETAILED DESCRIPTION

Figure 3:
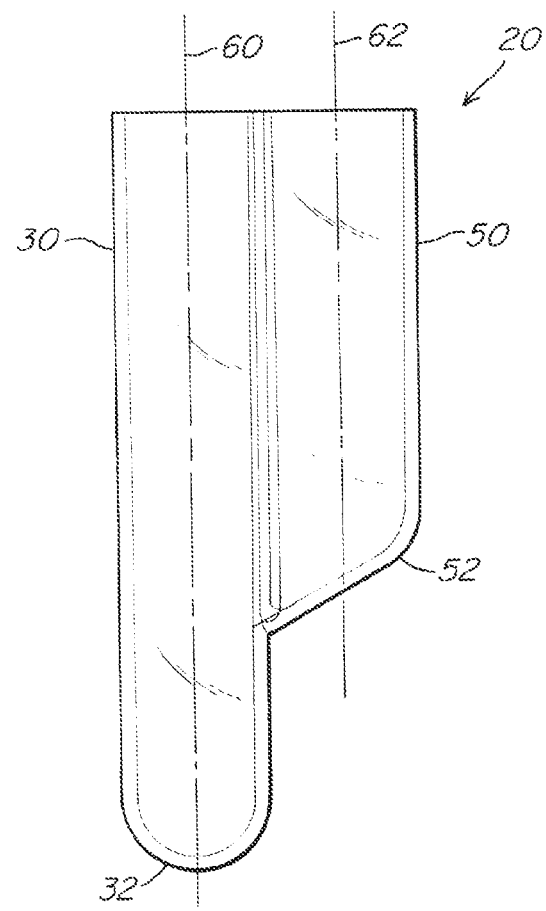
FIG. 3 is a side view of the tube illustrated in FIG. 2.

Aspects of the invention are directed to a device for separating portions of a sample, and methods for using the device to separate portions of a sample.

As discussed above, there are a variety of known devices to separate agglomerated material or clumps of material from a sample that includes a liquid component. Applicant recognized that some of these prior devices may lead to undesirable loss of the liquid portion of the sample in some cases. For example, as shown in FIG. 1, as the filter element 12 moves down the tube 10, the liquid portion of the sample 16 passes through the filter element, leaving the solid phase portion 18 at the bottom of the tube 10. Although this device separates some of the liquid 16 from the solid phase 18, some of the liquid 16 remains intermixed with the solid phase 18 below the filter element 12. With this particular type of device, it may be difficult to separate and thus recover the remaining amount of the liquid 16. It may not be possible to recover this liquid portion without removing the filter element from the tube 10 and employing further separation techniques to separate the solid phase 18 from the remaining liquid 16. Aspects of the present invention are directed to a device for separating agglomerated material or clumps of material out from a sample where there is little and/or substantially no loss of the liquid portion of the sample during the separation process.

Aspects of the invention employ a tube for separating a liquid portion of a sample where the tube includes a first opening for dispensing an unseparated sample including liquid and solid material into the tube and a second opening for removing a separated liquid component from the tube after the agglomerated material or clumps of material have been separated out from the liquid component.

As set forth in greater detail below, aspects of the present invention involve a tube for separating a liquid portion of a sample where the tube includes a slit arranged so that after the sample is dispensed into the tube, a portion of the sample passes through the slit while material in the sample having a size larger than the slit does not pass through the slit.

It should be appreciated that it is contemplated that the tube may be used to separate a variety of types of samples, as the invention is not limited in this respect. For example, as discussed above, in one embodiment, the tube may be configured to separate a blood sample such that fibrin clots and/or platelet clots may be separated from serum portions of the sample. In another embodiment, the tube may be configured to separate other types of samples, such as, but not limited to other bodily fluids, as well as other fluids, such as but not limited to samples including reagents or other liquid as well as beads or other solid material to be separated from the liquid (e.g., as in the case of beads having attached DNA or other genomic components in a liquid), and so on. As discussed in greater detail below, the slit in the tube may be sized for a particular application based upon the type of sample and the size of the material that is desired to be separated in the sample.

Turning to the drawings, it should be appreciated that the drawings illustrate various components and features which may be incorporated into various embodiments that incorporate aspects of the invention. For simplification, some of the drawings may illustrate more than one optional feature or component. However, aspects of the invention are not limited to the specific embodiments disclosed. It should be recognized that aspects of the invention encompass embodiments which may include only a portion of the components illustrated in any one figure, and/or may also encompass embodiments combining components illustrated in multiple different drawings.

FIGS. 2-7 illustrate a tube 20 for separating a sample according to one embodiment of the present invention. The tube 20 has a chamber 30 with a closed bottom 32 and a sidewall 34 extending upwardly from the bottom 32 and defining a chamber opening 36. A sample inlet branch 50 is coupled to the chamber and has a sidewall 54 defining a sample inlet branch opening 56. As discussed in greater detail below, the tube 20 has a slit 40 positioned between the chamber 30 and the sample inlet branch 50.

A sample may be placed into the tube 20 through the sample inlet branch opening 56, e.g., by a pipette or other suitable arrangement placing a blood sample in the sample inlet branch opening 56. Once within the sample inlet branch 50, a portion of the sample (such as blood serum or other liquid component containing solid material smaller than the slit 40) passes through the slit 40 and into the chamber 30. Material in the sample having a size larger than the slit, such as blood clots, may remain within the sample inlet branch 50. Thus, the liquid portion of the sample having a size smaller than the slit 40 is separated from the larger material. This liquid portion collects in the chamber 30 and may be removed from the chamber 30 through the chamber opening 36, e.g., by a pipette aspirating the liquid portion.

In one embodiment, it is desirable for the slit 40 to be constructed such that the liquid portion of the sample is still able to pass through the slit 40 even after material, such as blood clots, collects at the bottom of the sample inlet branch 50. For example, in one embodiment, the slit 40 extends along a substantial length of the sample inlet branch 50 and in one embodiment, the slit extends along a majority of the length of the branch 50. In this respect, material that has collected at the bottom 52 of the branch 50 may be less likely to obstruct the entire slit 40. Thus, in some cases, liquid will still be able to pass through the upper portion of the slit 40 and pass into the chamber 30. In other cases, relatively large size material that collects above the bottom 52 (e.g., material that is suspended in the sample or floats at the sample top surface) will not impede the passage of liquid material, which may pass through the slit 40 near the bottom 52. In the illustrated embodiment, the slit 40 extends to the bottom 52 of the branch 50 and up to the sample inlet branch opening 56. It may be desirable for the slit 40 to extend down close to the bottom 52 of the branch 50 to minimize the amount of liquid that is able to pool or otherwise collect at the bottom 52 of the branch 50. In certain embodiments, it may be desirable for the slit 40 to extend close to the branch opening 56 so that the liquid portion of the sample is still able to pass through the slit 40 even after a substantial amount of material has collected at the bottom 52 of the branch 50.

As shown in FIGS. 3 and 5, in one embodiment, the bottom 52 of the sample branch 50 is sloped for liquid to drain towards the slit 40. As also illustrated in the embodiment shown in FIGS. 2-7, the bottom of the sample inlet branch and the bottom of the chamber are substantially rounded. It should be appreciated that in another embodiment, the bottom 52 of the sample branch 50 may be shaped differently, and may for example be substantially flat, curved or irregular shaped. Furthermore, it should also be recognized that the bottom 32 of the chamber may either be configured the same as or different than the bottom 52 of the sample inlet branch as the invention is not so limited.

The shape of the tube 20 for separating a sample may also vary, as the invention is not limited in this respect. In the embodiment illustrated in FIGS. 2-7, the chamber sidewall 34 is substantially cylindrical shaped and the sample inlet branch sidewall 54 is also substantially cylindrical shaped. It is also contemplated that the chamber sidewall 34 and/or the branch sidewall 54 may be rectangular shaped, square shaped, or irregular shaped. Furthermore, the shape of the chamber 30 may be configured as either the same shape or a different shape than the sample inlet branch 50.

In the embodiment illustrated in FIGS. 2-7, the tube 20 is bifurcated such that the sample inlet branch 50 extends outwardly from the chamber sidewall 34. Furthermore, in the embodiment illustrated in FIGS. 2-7, the chamber 30 and the sample inlet branch 50 both have a longitudinal axis 60, 62, and the longitudinal axis 62 of the sample inlet branch 50 is substantially parallel to the longitudinal axis 60 of the chamber 50. As discussed in greater detail below, in another embodiment, the tube 20 may not be bifurcated, and/or the longitudinal axes 60, 62 of the chamber 30 and branch 50 may not be parallel.

FIGS. 5-7 illustrate one embodiment of a slit 40 in greater detail. In this particular embodiment, the slit 40 is tapered such that the width of the slit near the sample inlet branch opening 56 is greater than the width of the slit 40 near the bottom 52 of the sample inlet branch. In another embodiment, the slit may have a substantially constant width along its length, and in yet another embodiment, the slit 40 may taper in the opposite direction such that the width of the slit 40 is greater towards the bottom 52 of the sample inlet branch 50.

Figure 4:
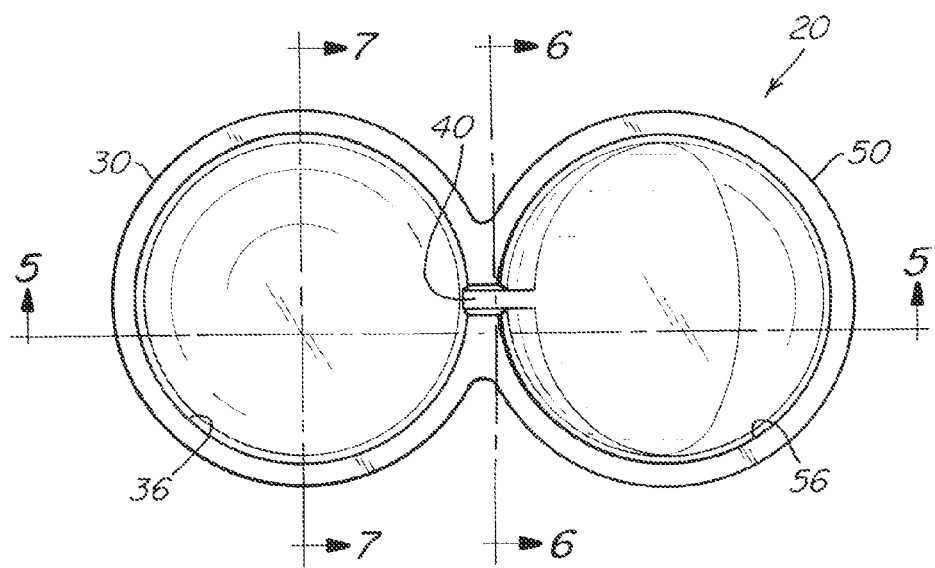
FIG. 4 is a top view of the tube illustrated in FIG. 2.

As illustrated in the embodiment of FIG. 4, the sample inlet branch opening 56 is connected to the chamber opening 36. In this embodiment, the slit 40 extends up to the branch opening 56 and is positioned between the branch opening 56 and the chamber opening 36 such that it fluidly connects these two openings. In another embodiment, the sample inlet branch opening 56 may be spaced apart and distinct from the chamber opening 36.

The size of the tube 20 may vary as the invention is not limited in this respect. The size of the chamber 30 and sample inlet branch 50 may vary based upon the volume of sample to be collected and separated within the tube. In one illustrative embodiment, the volume of the sample inlet branch 50 is less than the volume of the chamber 30. This may be desirable where the sample being separated has a larger volume of liquid that passes through the slit in comparison to the volume of material that will remain in the branch 50. In one embodiment, the volume of the chamber 30 is at least double the volume of the sample inlet branch 50. In another embodiment, the volume of the branch 50 may be approximately the same as the volume of the sample inlet branch 50, and in yet another embodiment, the volume of the branch 50 may be greater than the volume of the chamber 30. In one embodiment, the volume of the chamber may be between approximately 100 microliters and 475 milliliters (ml). In one embodiment, the maximum volume of the chamber 30 is approximately 200 ml. In another embodiment, the volume of the chamber 30 is between approximately 5-10 ml. In yet another embodiment, the volume of the chamber may be approximately 10 ml-100 ml.

The orientation of the slit 40 relative to other components of the tube 20 may vary according to different embodiments of the present invention. In the embodiment illustrated in FIGS. 2-7, the chamber 30 has a longitudinal axis 60 and at least a portion of the slit 40 is positioned vertically such that the slit is substantially parallel with the longitudinal axis 60 of the chamber 30. In this particular illustrative embodiment, the slit 40 is also substantially parallel with the chamber sidewall 34. As discussed in greater detail below, in another embodiment, the slit 40 may not be parallel with a longitudinal axis 60 of the chamber 30.

Figure 8:
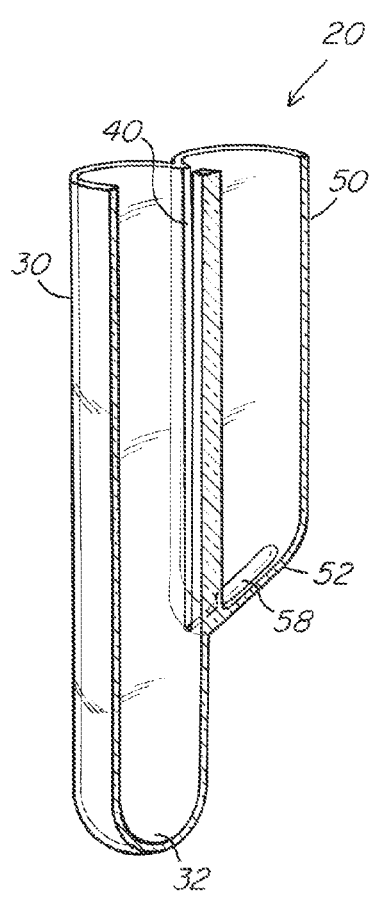
FIG. 8 is a perspective cross-sectional view similar to FIG. 5 illustrating another embodiment of the present invention.

FIG. 8 illustrates another embodiment that is similar to the above-described embodiment shown in FIGS. 2-7 except that the tube 20 shown in FIG. 8 further includes a groove 58 in the bottom 52 of the sample inlet branch 50 that is configured to guide the liquid portion of the sample toward the slit 40. In this particular embodiment, the groove 58 extends along a substantial portion of the bottom 52.

Figure 9:
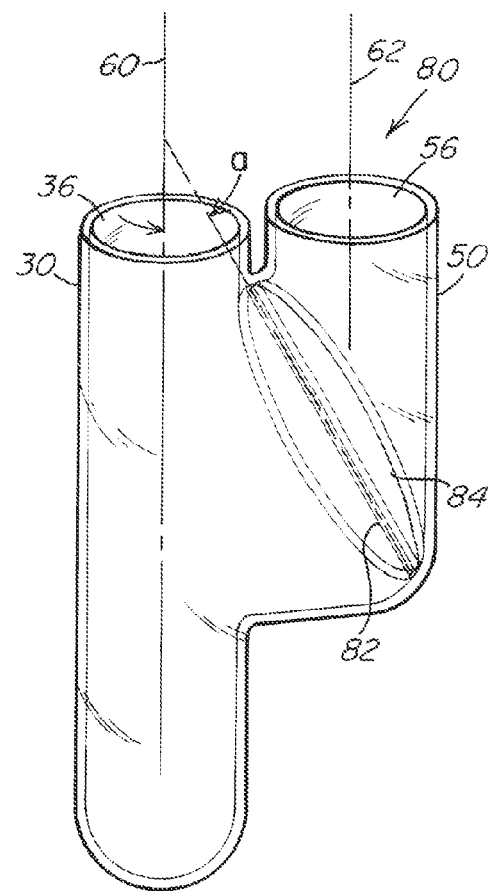
FIG. 9 is a front view of a tube for separating a sample according to another embodiment of the present invention.

FIG. 9 illustrates yet another embodiment of a tube 80 for separating a sample. The tube 80 has a chamber 30 and a sample inlet branch 50 which are similar to the embodiment illustrated in FIGS. 2-7. The tube 80 also has a slit 82 positioned between the chamber 30 and the sample inlet branch 50. The slit 82 is formed into a plate component 84 and the slit 82 is arranged so that a liquid portion in the branch 50 passes through the slit 82 and into the chamber 30. In this illustrative embodiment, the slit is not substantially parallel with the longitudinal axes 60, 62 of either the chamber 30 or the branch 50. As illustrated, at least a portion of the slit 82 is positioned at a diagonal such that the slit 82 is neither substantially parallel or substantially perpendicular with the longitudinal axis of the chamber 30. In this embodiment, a dashed line extends up from the slit 82 up to the longitudinal axis 60 of the chamber 30 and illustrates the angle A between the slit 82 and the longitudinal axis 60. In one particular embodiment, the angle A is between approximately 20 degrees-60 degrees. In one embodiment, the angle A is approximately 30 degrees.

Figure 10:
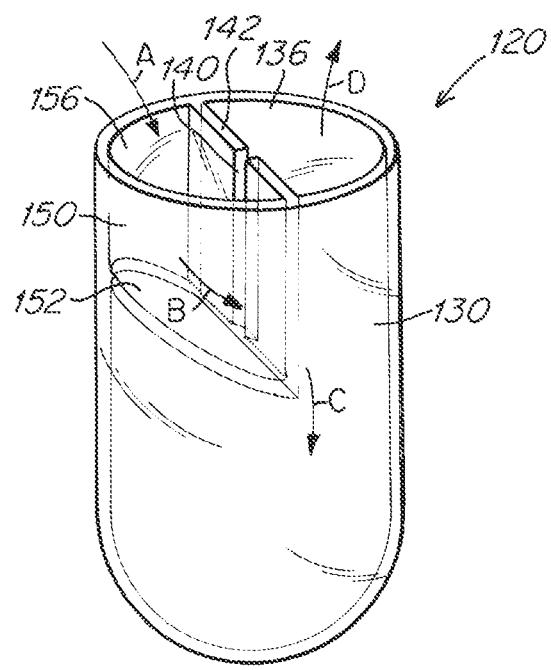
FIG. 10 is a front perspective view of a tube for separating a sample according to yet another embodiment of the present invention.
Figure 11:
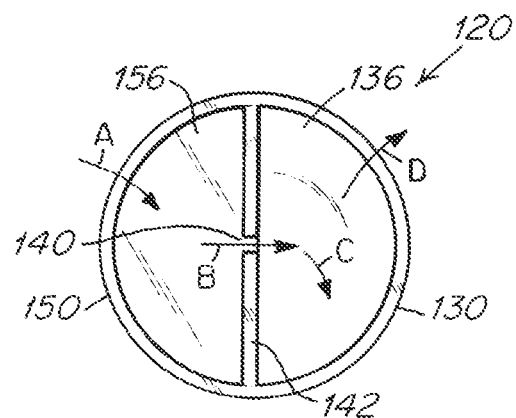
FIG. 11 is a top view of the tube illustrated in FIG. 10.

FIGS. 10-11 illustrate yet another embodiment of a tube 120 for separating a sample. The tube 120 has a chamber 130 and a sample inlet branch 150 which together form a cylindrical shaped component with a slit 140 positioned between the chamber 130 and the sample inlet branch 150. The slit is arranged so that liquid can pass through the slit from the sample inlet branch 150 into the chamber 130. In this embodiment, the slit 140 is formed into to flat plate component 142 which is positioned within the cylindrical shaped component. It should be appreciated that in another embodiment the tube 120 may be shaped and configured differently.

As previously mentioned, a sample may be dispensed into the tube 120 through the sample inlet branch opening 156 (see arrow A). Once within the sample inlet branch 150, a portion of the sample passes through the slit 140 (see arrow B) and into the chamber 130 (see arrow C). In the embodiment illustrated in FIGS. 10-11, the bottom 152 of the branch 150 is a substantially flat surface that is sloped towards the slit 140. Material in the sample having a size larger than the slit remains within the sample inlet branch 150. Thus, the liquid portion of the sample having a size smaller than the slit is separated from the larger material. This liquid portion collects in the chamber 130 and may be removed from the chamber 130 through the chamber opening 136 (see arrow D). It should be appreciated that material collected in the sample inlet branch 150 may be collected for further processing and/or discarded.

In one embodiment, the tube for separating a sample is configured to be employed in high volume and/or automated liquid sample processing techniques. For example, there may be an array of multiple tubes for separating samples. A plurality of automated pipetting instruments may be aligned with the tubes and the system may be configured to simultaneously dispense a sample into the sample inlet branches of the plurality of tubes. The sample is separated using the above-described slit positioned in each of the tubes, and thereafter, at least a portion of the sample is removed from one of the tube chambers. In one embodiment, a pipetting instrument is used to aspirate the sample portion out of the chamber.

The size of the tube may vary as the invention is not limited in this respect. In one embodiment, the chamber is between approximately 5 cm-25 cm in length and the sample inlet branch is approximately 2 cm-15 cm in length.

In one embodiment, the width of the slit is approximately 1 mm-5 mm. In one embodiment, the width of the slit is less than 5 mm. In another embodiment, the width of the slit is less than 2 mm, and in yet another embodiment, the width of the slit is less than 1.25 mm. In one tapered slit embodiment, the width of the slit may double from the narrow end of the slit to the widest section of the slit. For example, in one embodiment, the tapered slit may have a width of approximately 1 mm at one end and a width of approximately 2 mm at the other end of the slit. It should be appreciated that in one embodiment, the tapered slit may be substantially v-shaped. The angle of the taper may vary, and in one embodiment, the angle of the taper may vary from approximately 1-2 degrees, although other angles are possible.

It should be appreciated that the slit may be configured based upon the size of the material that is desired to be separated or removed from the sample. The width of the slit may be configured to be smaller than the size of the agglomerated material, clumps of material or other components that will be separated out from smaller components of the sample.

The tube may be formed from a variety of different types of materials and manufacturing techniques. The tube may be made from a material such as, but not limited to, glass, metal or plastic, such as polystyrene. The tube may be formed of either transparent or opaque materials. In one embodiment, the chamber and sample inlet branch are integrally formed. In another embodiment, the chamber and branch may be separately formed and thereafter coupled. In one embodiment, the tube is molded.

It should also be recognized that in one embodiment, the tube for separating a sample may include no movable components. In particular, the tube may rely on gravity to move portions of the sample from the top of the tube, through the slit and to the bottom of the chamber.

It should be appreciated that various embodiments of the present invention may be formed with one or more of the above-described features. The above aspects and features of the invention may be employed in any suitable combination as the present invention is not limited in this respect. It should also be appreciated that the drawings illustrate various components and features which may be incorporated into various embodiments of the present invention. For simplification, some of the drawings may illustrate more than one optional feature or component. However, the present invention is not limited to the specific embodiments disclosed in the drawings. It should be recognized that the present invention encompasses embodiments which may include only a portion of the components illustrated in any one drawing figure, and/or may also encompass embodiments combining components illustrated in multiple different drawing figures.

It should be understood that the foregoing description of various embodiments of the invention are intended merely to be illustrative thereof and that other embodiments, modifications, and equivalents of the invention are within the scope of the invention recited in the claims appended hereto.

What is claimed is:

1. A tube for separating a blood clot from serum in a blood sample, comprising:
    a chamber with a closed bottom and a sidewall extending upwardly from the chamber bottom, the sidewall defining a chamber opening for accessing a portion of the sample in the chamber;
    a sample inlet branch coupled to the chamber, the sample inlet branch having a sidewall defining a sample inlet branch opening for receiving a sample into the sample inlet branch, and the sample inlet branch having a bottom; and
    a slit positioned between the chamber and the sample inlet branch and extending from near the sample inlet branch opening toward the sample inlet branch bottom, the slit being tapered such that a width of the slit near the sample inlet branch opening is greater than a width of the slit near the bottom of the sample inlet branch,
    wherein the slit is sized and positioned so that, with a blood sample that includes serum and a blood clot having a size larger than the slit located in the sample inlet branch, a portion of the serum passes through the slit and into the chamber relying on gravity alone and the blood clot remains in the sample inlet branch.

2. The tube of claim 1, wherein the slit extends along substantially the entire length of the sample inlet branch.

3. The tube of claim 1, wherein the chamber and the sample inlet branch together form a single cylindrical shaped component.

4. The tube of claim 1, wherein the slit extends from the sample inlet branch opening toward the bottom of the chamber.

5. The tube of claim 1, wherein the slit extends to the sample inlet branch bottom.

6. The tube of claim 5, wherein the bottom of the sample inlet branch is substantially rounded.

7. The tube of claim 5, wherein the bottom of the sample inlet branch is sloped for draining a portion of the blood sample toward the slit.

8. The tube of claim 5, further providing a groove in the bottom of the sample inlet branch, the groove comprising an indentation lying below a bottom surface of the sample inlet branch, and the groove being configured to guide a portion of the blood sample toward the chamber while preventing blood clots in the blood sample of a certain size from entering the groove.

9. The tube of claim 1, wherein the chamber sidewall is substantially cylindrical shaped, and the sample inlet branch sidewall is substantially cylindrical shaped.

10. The tube of claim 1, wherein the tube is bifurcated such that the sample inlet branch extends outwardly from the chamber sidewall.

11. The tube of claim 1, wherein the chamber has a longitudinal axis, and wherein at least a portion of the slit is substantially parallel with the longitudinal axis of the chamber.

12. The tube of claim 1, wherein the chamber has a longitudinal axis and the sample inlet branch has a longitudinal axis, wherein the longitudinal axis of the sample inlet branch is substantially parallel to the longitudinal axis of the chamber.

13. The tube of claim 1, wherein the slit is substantially parallel with the chamber sidewall.

14. The tube of claim 1, wherein the chamber has a longitudinal axis, and wherein the slit is positioned at a diagonal relative to the longitudinal axis of the chamber.

15. The tube of claim 1, wherein the sample inlet branch opening is fluidly connected to the chamber opening by the slit.

16. The tube of claim 1, wherein the width of the slit is less than 2 mm.

17. The tube of claim 1, wherein the width of the slit is less than 1.25 mm.

18. The tube of claim 1, wherein the width of a first end of the slit is twice the width of a second opposite end of the slit, and wherein the distance from the first end to the sample inlet branch opening is less than the distance from the second end to the sample inlet branch opening.

19. The tube of claim 1, wherein an angle of a taper of the slit is 1 to 2 degrees.

* * * * *